United States Patent
Fontenot et al.

(10) Patent No.: US 6,171,695 B1
(45) Date of Patent: *Jan. 9, 2001

(54) THIN ABSORBENT PADS FOR FOOD PRODUCTS

(75) Inventors: Monica Carlise Fontenot, Marietta, GA (US); Fung-Jou Chen, Appleton, WI (US)

(73) Assignee: Kimberly-Clark Worldwide, Inc., Neenah, WI (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/858,680

(22) Filed: May 19, 1997

Related U.S. Application Data (63) Continuation-in-part of application No. 08/614,420, filed on Mar. 8, 1996, now abandoned, which is a continuation-in-part of application No. 08/310,186, filed on Sep. 21, 1994, now abandoned.

(51) Int. Cl.[7] .......................... B32B 29/00; B32B 29/06; B65D 81/26
(52) U.S. Cl. .......................... 428/337; 428/339; 428/340; 428/535; 428/537.5; 206/204; 206/205
(58) Field of Search .................. 428/174, 535, 428/534, 537.1, 537.5, 533, 311.71, 311.91, 337, 339, 340, 74; 156/306.3; 162/205; 426/124, 129; 206/204, 205

(56) References Cited

U.S. PATENT DOCUMENTS

| | | | |
|---|---|---|---|
| 3,026,209 | 3/1962 | Niblack et al. | 99/174 |
| 3,338,992 | 8/1967 | Kinney | 264/24 |
| 3,339,550 | 9/1967 | Van Haaften | 128/290 |
| 3,341,394 | 9/1967 | Kinney | 161/72 |
| 3,375,827 | 4/1968 | Bletzinger et al. | 128/290 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,700,623 | 10/1972 | Keim | 260/80.3 R |
| 3,772,076 | 11/1973 | Keim | 117/155 R |
| 3,802,817 | 4/1974 | Matsuki et al. | 425/66 |
| 3,821,068 | 6/1974 | Shaw | 162/111 |
| 3,849,241 | 11/1974 | Butin et al. | 161/169 |
| 3,855,158 | 12/1974 | Petrovich et al. | 260/2 BP |
| 3,899,388 | 8/1975 | Petrovich et al. | 162/164 |

(List continued on next page.)

FOREIGN PATENT DOCUMENTS

| | | |
|---|---|---|
| 1035186 | 7/1978 | (CA) . |
| 2013905 | 10/1990 | (CA) . |
| 1329573 | 5/1994 | (CA) . |
| 0241263 | 10/1987 | (EP) . |
| 2303647 | 2/1997 | (GB) . |
| 92/04254 | 3/1992 | (WO) . |
| 92/18398 | 10/1992 | (WO) . |
| 93/20950 | 10/1993 | (WO) . |
| 96/09435 | 3/1996 | (WO) . |

* cited by examiner

Primary Examiner—Blaine Copenheaver
Assistant Examiner—Cheryl Juska
(74) Attorney, Agent, or Firm—Douglas H. Tulley, Jr.

(57) ABSTRACT

Thin absorbent food pads with a bulk under 0.5 cm are provided having an insulation layer and from 3 to 30 sheets of compressed wet resilient cellulosic material wherein the absorbent pad has an absorbent capacity of at least 10 grams fluid per gram absorbent material and which expands in volume by at least 50%, relative to dry volume, upon wetting. The thin absorbent pads may be provided by calendering the insulation layer and cellulosic sheets under a force of about 100 to 1500 pounds per linear inch, thereby reducing the bulk of the pad by 30 to 60% and creating a pad which will significantly expand upon wetting to achieve an aqueous absorbent capacity of about 0.85 grams fluid per square centimeter (5.5 g/square inch).

25 Claims, 3 Drawing Sheets

U.S. PATENT DOCUMENTS

| | | | |
|---|---|---|---|
| 4,041,203 | 8/1977 | Brock et al. | 428/157 |
| 4,129,528 | 12/1978 | Petrovich et al. | 260/823 |
| 4,147,586 | 4/1979 | Petrovich et al. | 162/135 |
| 4,191,609 | 3/1980 | Trokhan | 162/113 |
| 4,222,921 | 9/1980 | Van Eenam | 260/29.6 H |
| 4,275,811 | 6/1981 | Miller | 206/204 |
| 4,321,997 | 3/1982 | Miller | 206/204 |
| 4,340,563 | 7/1982 | Appel et al. | 264/518 |
| 4,382,507 | 5/1983 | Miller | 206/204 |
| 4,388,075 | 6/1983 | Mesek et al. | 604/385 |
| 4,410,578 | 10/1983 | Miller | 428/117 |
| 4,440,597 | 4/1984 | Wells et al. | 162/111 |
| 4,500,316 | 2/1985 | Damico | 604/389 |
| 4,529,480 | 7/1985 | Trokhan | 162/109 |
| 4,631,933 | 12/1986 | Carey, Jr. | 66/192 |
| 4,637,859 | 1/1987 | Trokhan | 162/109 |
| 4,650,481 | 3/1987 | O'Connor et al. | 604/380 |
| 4,699,823 | 10/1987 | Kellenberger et al. | 428/219 |
| 4,756,939 | 7/1988 | Goodwin | 4218/74 |
| 4,865,855 | 9/1989 | Hansen et al. | 426/124 |
| 4,891,957 | 1/1990 | Strack et al. | 66/192 |
| 4,929,480 | 5/1990 | Midkiff et al. | 428/35.6 |
| 4,935,276 | 6/1990 | Pawlowski et al. | 428/35.7 |
| 4,938,754 | 7/1990 | Mesek | 604/385.2 |
| 4,940,464 | 7/1990 | Van Gompel et al. | 604/396 |
| 4,940,621 | 7/1990 | Rhodes et al. | 428/137 |
| 5,048,589 | 9/1991 | Cook et al. | 162/109 |
| 5,069,548 | 12/1991 | Boehnlein | 356/376 |
| 5,087,324 | 2/1992 | Awofeso et al. | 162/111 |
| 5,116,661 | 5/1992 | Matsubara | 428/198 |
| 5,129,988 | 7/1992 | Farrington, Jr. | 162/123 |
| 5,145,727 | 9/1992 | Potts et al. | 428/198 |
| 5,147,343 | 9/1992 | Kellenberger | 604/368 |
| 5,169,706 | 12/1992 | Collier, IV et al. | 428/152 |
| 5,176,930 | 1/1993 | Kannankeril et al. | 426/124 |
| 5,178,931 | 1/1993 | Perkins et al. | 428/198 |
| 5,188,885 | 2/1993 | Timmons et al. | 428/198 |
| 5,190,563 | 3/1993 | Herron et al. | 8/120 |
| 5,192,606 | 3/1993 | Proxmire et al. | 428/284 |
| 5,223,096 | 6/1993 | Phan et al. | 162/158 |
| 5,240,562 | 8/1993 | Phan et al. | 162/158 |
| 5,336,373 | 8/1994 | Scattolino et al. | 162/116 |
| 5,364,382 | 11/1994 | Latimer et al. | 604/378 |
| 5,386,595 | 2/1995 | Kuen et al. | 2/400 |
| 5,387,385 * | 2/1995 | Murji et al. | 264/160 |
| 5,399,412 | 3/1995 | Sudall et al. | 428/153 |
| 5,409,768 | 4/1995 | Dickenson et al. | 428/283 |
| 5,411,636 | 5/1995 | Hermans et al. | 162/109 |
| 5,429,686 | 7/1995 | Chiu et al. | 139/383 A |
| 5,486,166 | 1/1996 | bishop et al. | 604/366 |
| 5,490,846 | 2/1996 | Ellis et al. | 604/366 |
| 5,492,598 | 2/1996 | Hermans et al. | 162/113 |
| 5,510,001 | 4/1996 | Hermans et al. | 162/113 |
| 5,510,002 | 4/1996 | Hermans et al. | 162/113 |
| 5,817,085 | 10/1998 | Widlund et al. | 604/379 |
| 5,877,097 | 3/1999 | West et al. | 442/327 |

THIN ABSORBENT PADS FOR FOOD PRODUCTS

This application is a continuation-in-part of application Ser. No. 08/614,420, entitled "WET-RESILIENT WEBS AND DISPOSABLE ARTICLES MADE THEREWITH" and filed in the U.S. Patent and Trademark Office on Mar. 8, 1996 now abandoned, which is a continuation-in-part of application Ser. No. 08/310,186 filed on Sep. 21, 1994, now abandoned. The entirety of this application is hereby incorporated by reference.

FIELD OF THE INVENTION

The present invention relates to absorbent articles for food products.

BACKGROUND OF THE INVENTION

Perishable foods, i.e. meats and poultry, are commonly sold in packaged form with an absorbent pad within the packaging to absorb any standing fluids. The absorbent pads are commonly placed on a rigid or semi-rigid support layer such as, for example, a foam tray. The meat or other product is then placed upon the absorbent pad and the entire package is wrapped in a protective wrap. Typically the package is wrapped with a transparent plastic wrap in order to allow the ultimate consumer to view the product while it is contained in the disposable, sanitary package. In this regard the absorbent pad soaks up blood or other fluids that may escape from the meat or other packaged product. Food packages of this type are generally described in U.S. Pat. No. 4,275,811 to Miller. Absorbing free or standing fluids serves several important functions such as, for example, keeping the packaged product in an aesthetically pleasing condition, reducing the risk of fluids escaping from the package, extending the shelf-life of the product and reducing the mess and clean-up on the part of the consumer once the package is opened and its contents removed.

Maintaining the fluids in a sanitary and manageable state is particularly important since leakage of such fluids not only creates unwanted mess but can cause potentially serious health concerns. In this regard bacterial growth is more readily supported by free standing fluids exuded from meat and poultry than by the products themselves. Rapid growth of bacteria resulting from standing fluids can considerably shorten the shelf-life of the packaged product by contaminating the packaged product by reverse migration of the fluids or by simply creating unpleasant odors. Moreover, contamination from bacteria or other organisms which may exist within such fluids can create significant health hazards, most notably with salmonella from poultry products. These potential health hazards have caused many grocers to completely stop butchering poultry products on-site. Grocers now commonly have such products prepared and packaged at a remote site such that the grocer receives the meat in a sanitary package. Of course it naturally follows that the benefits of off-site packaging is considerably reduced or eliminated if fluids from within the packaged products frequently escape therefrom. Therefore, significant importance is placed on the absorbent pad's ability to both absorb and retain such fluids.

The initial absorbency as well as the extended retention of the fluids is important not only to grocers but to the ultimate consumer as well. Although bacteria, such as salmonella, are readily destroyed with proper cooking, if the fluids escape or are not properly contained they can contaminate other surfaces which allows the bacteria to be passed on to other foods or materials. Thus, an absorbent pad which maintains the fluid as well as its integrity provides a significant advantage to the ultimate consumer. However, existing meat and poultry pads commonly employ a mat of wood fluff or multiple plies of creped tissue, absorbents which readily lose their integrity upon absorbing fluids. Thus, such absorbent pads often require additional layers of material to enclose the absorbent. Moreover, existing pads also fail to continue absorbing fluid after first wetting out. A food pad that not only retains liquid from an initial insult but can continue, thereafter, to absorb fluid is highly desirable.

In addition, in order to ensure that the meat pad is capable of absorbing the blood and/or other fluids, excess absorbent capacity is typically employed. However, since the amount of fluid that may leak from the product varies considerably, the desired minimum absorbent capacity of the absorbent pads are often considerable. For example, meat pads are commonly expected to absorb in excess of 100 g of fluid. In an attempt to meet these absorbency requirements existing meat pads are bulky and often employ a thick mat of wadding or numerous sheets of creped tissue in a single pad. Moreover, to meet the high-end absorbent capacities, often pads will be placed over one another which has the disadvantage of increasing the labor needed for packaging as well as further increasing the bulk of the package. An absorbent pad which is capable of meeting the desired absorbency needs yet which overcomes such deficiencies is highly desirable.

In addition, it is common for grocers to offer "value" or "family" packs which contain larger portions of meat, commonly including in excess of 3 lbs. of meat. Thus, the absorbent pads need to be able to adequately absorb fluids while under load. Furthermore, even when the contents of the package are not as large, the desired absorbent capacity still should function adequately under increased loads since packages are commonly stacked in shipping and/or storage. In this regard meat pads employing wood fluff or multiple sheets of creped tissue lose their integrity and shape once wet and, further, the absorbency of the pad decreases considerably when under loads commonly experienced by such pads.

U.S. Pat. No. 4,321,997 to Miller recognizes the deficiencies of such pads and discloses an absorbent pad for food products which employs a spacer layer, such as a net-like thermoplastic foam, which is intended to maintain the separation between the bottom layer of the pad and the absorbent material. Miller teaches that the spacer layer desirably minimizes the compression of the absorbent material and the corresponding reduction in the ability of the mat to absorb liquids. Canadian Patent No. 1329573 to Rhodes also recognizes the problem absorbent pads experience absorbing and maintaining fluid under load. However, Rhodes seeks to solve this problem by employing an absorbent layer comprising a combination of cellulosic, thermoplastic and superabsorbent materials. Due to the combination of these various materials, Rhodes suggests that the material has better absorbent capacity under load. However, the absorbent pads described above require relatively expensive materials and/ or designs which do not adequately solve the absorbency problems.

Therefore, there exists a continued need for an improved absorbent pad which is both efficient and economical for use in disposable food packaging. There further exists a need for an absorbent pad which is capable of retaining a high percentage of its absorbent capacity while under loads experienced by food grade absorbent pads. There likewise exists a need for an absorbent pad which has reduced bulk yet which retains the desired level of absorbent capacity. In addition, there further exists a need for an absorbent pad having the desired absorbent capacity which is capable of maintaining fluids and also retaining its integrity over extended periods of time.

SUMMARY OF THE INVENTION

The aforesaid needs are fulfilled and the problems experienced by those skilled in the art are overcome by an absorbent pad of the present invention which comprises an insulation layer and an absorbent core of a plurality of sheets of compressed wet resilient cellulosic material. The absorbent core desirably has an aqueous absorbent capacity of at least 10 grams fluid per gram absorbent material and is capable of expanding at least 50% in volume, relative to the dry volume, upon absorbing liquid. The absorbent core may have a thickness under about 0.5 cm and may further have a ratio of absorbent capacity to volume of at least 1.25 grams fluid per cubic centimeter. In a further aspect the absorbent core may have an aqueous absorbent capacity of at least 13 grams fluid per gram absorbent material and the pad may have a bulk of about 0.38 cm. The absorbent core may comprise from 3 to about 30 compressed cellulosic sheets having a basis weight of between about 20 and 40 gsm. In a further aspect, the resilient cellulosic sheets may contain a wet strength agent and may also comprise one or more individual cellulosic sheets having a three-dimensional pattern imparted thereto. Desirably, the absorbent core expands at least about 100% in volume upon wetting and further expands substantially in bulk or thickness upon absorbing fluid.

In a further aspect of the present invention, the absorbent pad may comprise an insulation layer and an absorbent core which comprises a plurality of sheets of resilient cellulosic material wherein the absorbent pad has an aqueous absorbent capacity of at least 0.85 grams fluid per square centimeter and a bulk less than about 0.5 cm. Further, the absorbent pad may have a bulk of less than 0.3 cm and/or an absorbent capacity of at least about 0.9 grams per square cm. In still a further aspect, the absorbent pad may comprise a plurality of compressed sheets of resilient cellulosic material which retains at least 60% of its absorbency (gram liquid per gram fiber), under a load of 3 pounds, relative to its absorbency without a load. Additionally, the absorbent core may comprise a resilient cellulosic material wherein the absorbent core has a ratio of absorbent capacity (g fluid) to volume (cubic centimeter) of at least 1.8 g/cc. The absorbent pad may further have a volume of 130 square centimeters or less and an absorbent capacity of at least 100 g liquid.

In a further aspect of the invention, an absorbent pad for food products may be made by (i) forming a plurality of relatively low-density sheets of cellulosic material; (ii) compressing the sheets of cellulosic material under a pressure of at least 50 pli thereby increasing the density of the sheets and reducing the bulk or thickness of the sheets wherein the compressed sheets will expand upon absorbing fluid, and (iii) coupling the compressed sheets of cellulosic material with an insulation layer. The sheets of relatively low-density cellulosic material may either be compressed individually, with additional sheets of low-density cellulosic material and/or together with the insulation layer. The sheets of relatively low-density cellulosic material are desirably compressed under a pressure of about 100 to about 2000 pli and with sufficient force to reduce the pads bulk by about 30% to about 60%. In a further aspect, the absorbent core may be coupled to the barrier layer such as, for example, by mechanical crimping.

DETAILED DESCRIPTION OF THE INVENTION

Although the invention is described in the context of several specific configurations, it will be appreciated that further combinations or alterations of the embodiments discussed below may be made by one skilled in the art without departing from the spirit and scope of the present invention. In addition, although reference is often made with respect to absorbent meat pads, those skilled in the art will appreciate that other modifications may be made hereto to adapt the absorbent pad for use with other packaged products which are prone to leak or otherwise exude fluid therefrom.

The absorbent pad of the present invention can be shaped to conform to the desired packaging or container. The particular form of the food container and/or packaging itself may comprise any one of numerous forms known to those skilled in the art such as, for example, wrapped trays, cardboard boxes, plastic containers, sealable bags, etc. However, with respect to packaged meat and poultry, the absorbent pads are often placed over the central portion of a foam tray. Although rectangular configurations are most common, the actual dimensions of the tray can vary considerably depending on the nature and amount of product intended to be packaged. The absorbent pad may be sized to fit the tray as a single continuous unit or configured to overlay the tray in sections. For example, the absorbent pad material may be provided in roll form with a selected width, unwound and cut to the desired length. Those preparing the package can lay the strips of absorbent material adjacent one another as needed to conform to the dimension of a particular tray. Further, although the absorbent pad can be simply placed over a support tray prior to placing the product thereover, the absorbent pad may be permanently attached to the tray to prevent movement of the same in handling. As an example, the absorbent pad may be adhesively attached to the supporting layer. In addition, the absorbent pad may be made an integral part of the tray itself such as disclosed in commonly assigned U.S. Pat. No. 4,865,855 to Hansen et al.

Figure 1:
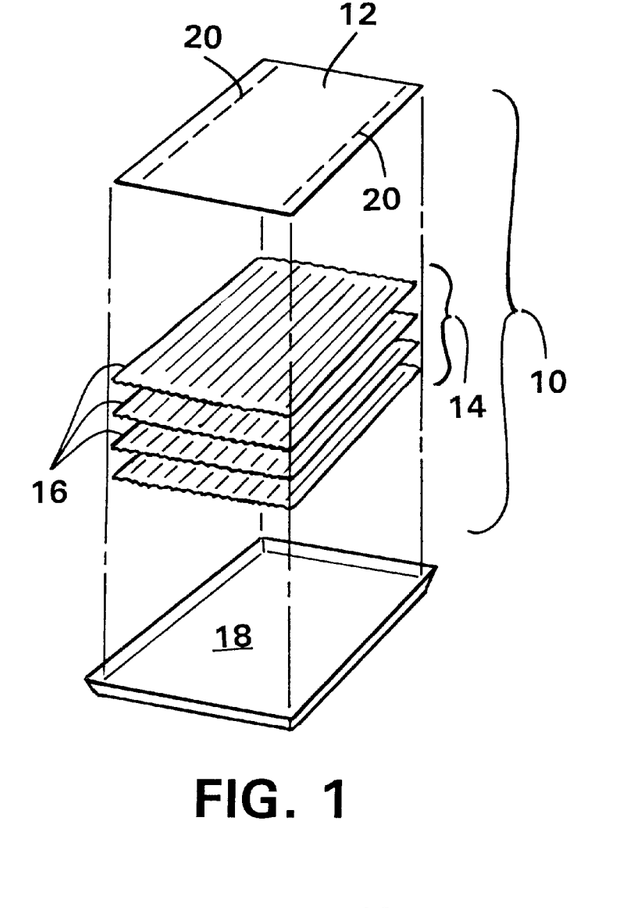
FIG. 1 is an exploded perspective view of a meat pad of the present invention and a support tray.

In a preferred embodiment, as shown in FIG. 1, an absorbent pad 10 of the present invention may comprise a top insulation layer 12 and an absorbent core 14. The absorbent pad is desirably placed on tray 18 or other packaging material with insulation layer 12 face-up. Thus, top insulation layer 12 functions to separate the product (not shown) from the absorbent core 14 thereby preventing loose fibers or other material from contacting the product. The term "insulation layer" as used herein simply refers to one or more components that act to separate the product from the compressed absorbent core. Desirably, top insulation layer 12 comprises a hydrophobic material compatible with the packaged product. The top insulation layer may comprise any one of numerous materials such as, for example, a plastic film, nonwoven web or a multilayer laminate. When used in connection with meats and other food products the insulation layer preferably comprises a food grade plastic. Top insulation layer 12 desirably comprises a plastic film such as, for example, a 0.005 inch thick non-perforated film of polyethylene. Although either liquid pervious or impervious layers may be used in connection with the present invention, the preferred design employs a non-perforated, liquid impervious barrier. With liquid impermeable barriers excess fluid escaping from the meat flows off the edges of the barrier layer and is absorbed. In addition, since portions of the plastic film will often remain visible to the ultimate consumer, the insulation layer may comprise one or more colors to achieve desired aesthetics and/or to mask standing fluid.

Absorbent core 14 may be attached directly to top insulation layer 12, however intermediate layers (not shown) may be positioned between top insulation layer 12 and absorbent core 14. The desired level of absorbent capacity of absorbent core 14 will vary with its intended application. Thus, the amount of absorbent material within the pad will likewise vary accordingly. In this regard it will be appreciated that as the amount of absorbent capacity of the pad increases, there is experienced in existing pads a corresponding increase in bulk. Further, it will also be appreciated that the absorbent capacity of existing pads under load is often considerably less than the corresponding absorbent capacity without load. However, although compression of cellulosic materials often results in a decrease in absorbent capacity of the individual sheets, it has been discovered that a compressed absorbent structure of wet resilient cellulosic materials is capable of meeting high-end absorbency requirements while having a decreased thickness or bulk. Thus, the present invention provides an absorbent pad which combines the desired level of absorbent capacity yet does so with minimal bulk and with good efficiency under load.

The compressed sheets 16 of absorbent core 14 comprise wet resilient absorbent materials which can be compressed under suitable conditions to provide materials of increased density that retain sufficient fluid handling and absorbing properties for use as a thin absorbent pad. When exposed to aqueous solutions and fluids, these materials expand and produce internal voids that absorb and hold fluid. The swelling associated with exposure to fluids is largely the resumption of the original low-density structure. Further, it has been found that the absorbent capacity of the compressed materials is generally less sensitive to loads applied thereto than many existing food pads. By using base sheets that have the desired wet resilience, bulk reduction by compression provides materials that are thin when dry but become thick when wet. As used herein a "wet resilient" absorbent material comprises a material wherein the volume expands upon absorbing liquid. The volume of the absorbent core, which comprises multiple sheets of the resilient absorbent material, desirably expands at least 50%, relative to the dry volume, when saturated or wetted out. Desirably the absorbent material is capable of increasing about 100% in volume or more upon wetting, and even more desirably capable of expanding from about 150 to 200% or more upon wetting.

The absorbent core 14 desirably comprises a plurality of absorbent layers or sheets 16 of compressed wet resilient cellulosic material. The absorbent pad desirably comprises 3 or more sheets of resilient cellulosic material and, more desirably, from 3 to about 30 sheets. The individual sheets may have a basis weight from about 20 to about 40 gsm (grams per square meter), and even more desirably a basis weight between about 25 to 30 gsm. The reduced thickness and increased density may be obtained by compressing the sheets individually or collectively as discussed in greater detail herein below. Thus, in one embodiment, the compressed individual sheets 16 can have an average density of about 0.075 g/cc or greater, and more desirably greater than about 0.15 g/cc. Desirably the absorbent core comprises a plurality of sheets 16 of throughdried high yield pulp fibers having a wet strength agent therein. However, other materials having the desired absorbent capacity and wet resilience may also be used in connection with the present invention.

Suitable absorbent materials that can be compressed to form wet resilient structures include absorbent cellulosic materials such as, for example, those disclosed in commonly assigned co-pending patent application Ser. No. 08/614,420 to Chen et al. filed Mar. 8, 1996 (hereinafter Chen '420); the entire contents of the aforesaid application is incorporated herein by reference. A further desirable attribute of the material of Chen '420 is the resistance of its structure to collapse when the sheet is saturated with fluid. This attribute of wet collapse resistance imparts a significant improvement in fluid handling properties to these fiber webs. The ability of such resilient compressed absorbent sheets to retain their integrity when saturated with fluid is an additional benefit of absorbent pads of the present invention. Exemplary absorbent materials useful for purposes of this invention are wet resilient fibers which may include, but are not limited to, high yield pulp fibers (further discussed below), flax, milkweed, abaca, hemp, cotton or any of the like that are naturally wet resilient or any wood pulp fibers that are chemically or physically modified, e.g. cross-linked or curled, that have the capability to recover after deformation in the wet state, as opposed to non-resilient fibers which remain deformed and do not recover after deformation in the wet state. Wet-resistant bonds are fiber-to-fiber bond sites that are resistant to disruption in the wet state resulting in improved wet tensile strength.

As used herein, "high yield pulp fibers" are those paper making fibers produced by pulping processes providing a yield of about 65 percent or greater, more specifically about 75 percent or greater, and still more specifically from about 75 to about 95 percent. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulphite pulps, and high yield kraft pulps, all of which leave the resulting fibers with high levels of lignin. The preferred high yield pulp fibers are characterized by being comprised of comparatively whole, relatively undamaged tracheids, high freeness (over 250 CSF), and low fines content (less than 25 percent by the Britt jar test). The amount of high yield pulp fibers in the relatively low density sheet can be at least about 10 dry weight percent or greater, more specifically about 30 dry weight percent or greater, still more specifically about 50 dry weight percent or greater, and up to 100 percent.

The resilient cellulosic sheets desirably employ an effective material to immobilize the bonds between the fibers in the wet state. Typically the means by which fibers are held together in paper and tissue products involve hydrogen and sometimes combinations of hydrogen bonds and covalent and/or ionic bonds. It is desirable to provide a material that will allow bonding of fibers in such a way as to immobilize the fiber-to-fiber bond points and make them resistant to disruption in the wet state. In this instance the wet state usually will mean when the product is exposed to water or other aqueous solutions, but also includes exposure to other fluids such as blood and other aqueous suspensions.

There are a number of materials commonly used in the paper industry to impart wet strength to paper and board that are applicable to this invention. These materials are known in the art as wet strength agents and are commercially available from a wide variety of sources. Any material that when added to a paper or tissue results in providing a tissue or paper with a wet strength: dry strength ratio in excess of 0.1 will, for purposes of this invention, be termed a wet strength agent. Typically these materials are termed either as permanent wet strength agents or as "temporary" wet strength agents. For the purposes of differentiating permanent from temporary wet strength, permanent will be defined as those resins which, when incorporated into paper or tissue products, will provide a product that retains more than 50% of its original wet strength after exposure to water for a period of at least five minutes. Temporary wet strength agents are those which show less than 50% of their original wet strength after exposure to water for five minutes. Both classes of material find application in the present invention, however, since permanent wet strength agents generally provide a more long-term wet resilience to the structure they are a preferred wet strength agent. The amount of wet strength agent added to the pulp fibers can be at least about 0.1 dry weight percent, more desirably about 0.2 dry weight percent or greater, and still more desirably from about 0.5 to about 3 dry weight percent based on the dry weight of the fibers.

The mechanism by which the wet strength is generated has little influence on the products of this invention as long as the essential property of generating water-resistant bonding at the fiber/fiber bond points is obtained.

Permanent wet strength agents that are useful in the present invention are typically water soluble, cationic oligomeric or polymeric resins that are capable of either cross-linking with themselves (homocross-linking) or with the cellulose or other constituent of the wood fiber. The most widely-used materials for this purpose are the class of polymer known as polyamide-polyamine-epichlorohydrin (PAE) type resins. These materials have been described in patents issued to Keim (U.S. Pat. Nos. 3,700,623 and 3,772,076) and are sold by Hercules, Inc., Wilmington, Del., as Kymene 557H. Related materials are marketed by Henkel Chemical Co., Charlotte, N.C. and Georgia-Pacific Resins, inc., Atlanta, Ga.

Polyamide-epichlorohydrin resins are also useful as bonding resins in this invention. Materials developed by Monsanto and marketed under the Santo Res label are base-activated polyamide-epichlorohydrin resins that can be used in the present invention. These materials are described in patents issued to Petrovich (U.S. Pat. No. 3,855,158; U.S. Pat. No. 3,899,388; U.S. Pat. No. 4,129,528 and U.S. Pat. No. 4,147,586) and van Eenam (U.S. Pat. No. 4,222,921). Although they are not as commonly used in consumer products, polyethylenimine resins are also suitable for immobilizing the bond points in the products of this invention. Other classes of permanent-type wet strength agents are exemplified by the aminoplast resins obtained by reaction of formaldehyde with melamine or urea.

With respect to the classes and the types of wet strength resins listed, it should be understood that this listing is simply to provide examples and that this is neither meant to exclude other types of wet strength resins, nor is it meant to limit the scope of this invention. Thus, although wet strength agents as described above find particular advantage for use in connection with in this invention, other types of bonding agents can also be used to provide the desired wet resiliency. They can be applied at the wet end or applied by spraying or printing, etc. after the web is formed or after it is dried.

The present invention can provide, through the plurality of compressed wet resilient sheets, an absorbent pad having an absorbency of at least 0.85 grams per square cm (5.5 g/in.$^2$), even more desirably an absorbency of at least 0.9 g/cm$^2$ (6 g/in.$^2$) or even 1.1 g/cm$^2$ (7 g/in.$^2$). Moreover, this absorbency may be achieved by a pad having a bulk of 0.5 cm (0.2 inches) or less and more desirably, by an absorbent pad having a bulk of less than about 0.38 cm (0.15 in.), 0.3 cm (0.12 in.) and even 0.25 cm (0.10 inches) or less. As used herein the term "bulk" refers to a measure of the thickness of a fabric as described in more detail herein below. The benefits achieved through the use of compressed wet resilient absorbent material may be expressed as a ratio of aqueous absorbent capacity (in gram liquid) to volume (cc). Thus, the present invention can provide a pad having an absorbent capacity (g fluid) to volume (cubic centimeters) ratio of at least 1.3 g/cc, 1.8 g/cc, and even more desirably of at least 2.0 g/cc or more.

In a further aspect, the aqueous absorbent capacity of the compressed absorbent core of this invention can be greater than about 10 grams of water per gram of absorbent material or greater, more desirably about 13 grams of water per gram of absorbent material or greater, and even more desirably about 15 grams of water per gram of absorbent material or greater. Thus, a particularly desirable embodiment of the present invention includes a meat pad having about 15–20 sheets of uncreped throughdried high yield pulp fibers and a wet strength agent which are collectively compressed such that the resulting sheets have thickness or bulk of less than about 0.38 cm (0.15 inches) and an absorbent capacity of at least 0.85 grams liquid per square centimeter. In addition, an improved absorbent pad is provided which has excellent absorbency retention under load and thereby provides an absorbent pad which is more efficient and economical than other pads. Thus, the absorbent core may comprise a resilient absorbent material which retains at least 60%, desirably at least 70%, of its absorbent capacity under a load of 1.36 Kg (3 lb.) relative to its absorbent capacity without load.

In making articles of the present invention, compression of the relatively low-density absorbent sheets can be carried out by a number of methods. In one embodiment, prior to compression, the low density sheets may be made such as, for example, in accord with Chen '420 desirably and have a density of about 0.2 g/cc or less, more desirably about 0.05 g/cc. It is desirable that, once formed, the relatively low density sheets containing a wet strength agent be dried without substantially reducing the number of wet-resilient interfiber bonds. Throughdrying, which is a common method for drying tissues and towels, is a preferred method of preserving the structure. Compression of the low-density absorbent sheets may be accomplished by compressing the sheets individually as described in U.S. patent application No. 08/773,797 filed Dec. 17, 1996 to Hollenberg et al., entitled "High-Density Absorbent Structure", the entire contents of which are incorporated herein by reference. Desirably, however, the compression of the low-density absorbent sheets is accomplished by collectively compressing a plurality of relatively low density (uncompressed) sheets. Passing multiple sheets simultaneously through one or more rollers or nips mechanically compresses the sheets in their entirety and the equipment used to do this is often termed a calender or supercalender. The densification resulting from calendering low density sheets depends upon the temperature, the pressure applied, the duration of the pressure and the number of sheets compressed. Suitable calendering pressures can be from about 50 to about 2000 pounds per linear inch (pli), desirably from about 100 to about 1400 pli. Suitable temperatures can be from about 20° C. to about 240° C., although desirably the calendering is done at ambient temperatures. The duration of calendering can be varied in conjunction with the nip pressure to produce the desired density, caliper sheet and/or bulk pad. Desirably the bulk of the (uncompressed) superposed sheets comprising the absorbent core is reduced by from 10% to 80% and, even more desirable, from about 30% to about 60%.

In addition to calendering or supercalendering of the relatively low density sheets, the sheets can be compressed using flat platen presses or fabric nips used to smooth and compact multi-wiper products as disclosed in U.S. Pat. No. 5,399,412 to Sudall et al. In this instance, the multi-ply wiper is carried on fabrics through a nip and the overall caliper of the multi-ply product is reduced. A similar process can be used to produce the sheets of the present invention.

The absorbent core 14 may be attached to top insulation layer 12 by one or more methods known in the art such as, for example, mechanical crimping, adhesively bonding or sewing. However, mechanical crimping is a preferred method of bonding top insulation layer 12 and absorbent core 14. Generally, bonding by mechanical crimping is achieved through coarse knurling on the crimping wheel. As an example the knurling may comprise a mesh pattern of crossed diagonal lines located at discrete locations about the wheel. In this regard, desirably absorbent core 14 is mechanically crimped to top barrier sheet 12 adjacent one or more edges of the pad. For example, the "stitch line" 20 created by the knurling of a mechanical crimper may run about 0.25 inches from and adjacent the length of opposed edges of pad 10. Generally, when mechanically crimping the top barrier layer and three or more resilient cellulosic sheets desirably pressures of about 900 to about 5000 pli (pounds per linear inch) are used.

Figure 2:
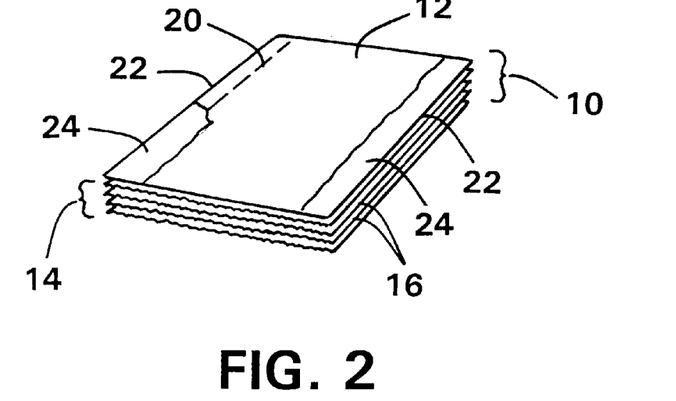
FIG. 2 is an angled view of an absorbent pad of the present invention having a sealed edge.

In a further aspect of the invention, and in reference to FIG. 2, the edges and/or structures of absorbent pad 10 may be sealed. A wax or other food grade sealant 24 may be applied to the pad between outer edge 22 and stitch-line 20. The molten wax may be applied to top insulating layer 12 such that it flows over the upper outer edge of the pad and also beneath top insulation layer 12 through the stitch-line 20. The molten wax may also flow through portions of the upper absorbent layers 16 adjacent top insulation sheet 12. The wax or other sealant may be applied in discrete locations or in continuous sections.

In addition, one skilled in the art will appreciate that additional layers such as, for example, a liquid pervious bottom layer and/or additional intermediate layers may be added to the absorbent pad to impart additional or improve the desired properties to the pad. Notably, a perforated bottom layer may be employed in combination with the top insulation layer to encase the absorbent core. Further, various additives or other materials may be included within the materials or disposed between layers to provide antibacterial properties, deodorizing capability, additional absorbent capacity or other desired properties.

Figure 3:
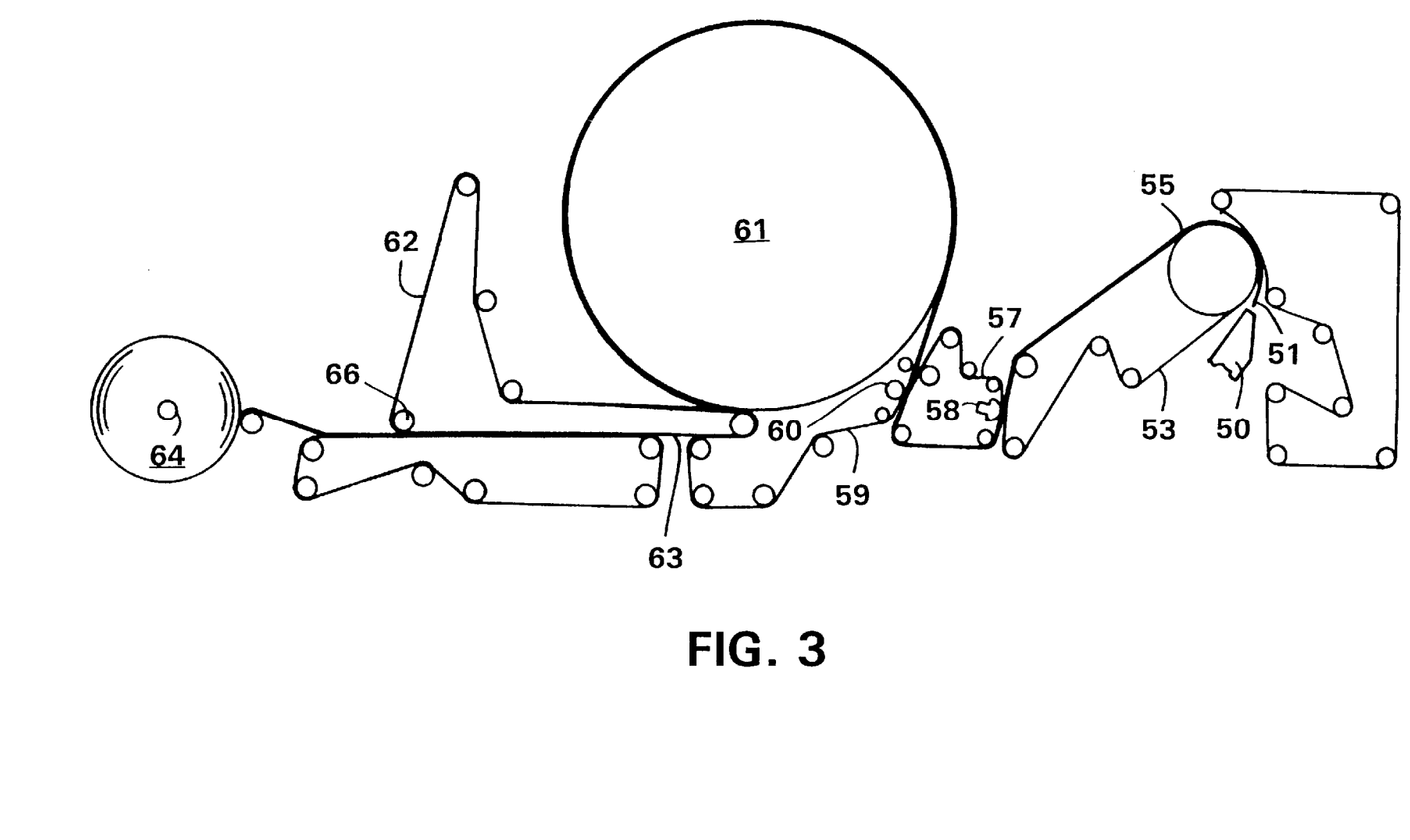
FIG. 3 is a schematic diagram of an uncreped through-dried paper making process useful for making compressable absorbent structures.

As an example, an absorbent pad of the present invention may be made in accord with the process set forth below. Referring to FIG. 3, a method for making throughdried paper sheets suitable for use with this invention is shown. For simplicity, the various tensioning rolls schematically used to define the several fabric runs are shown but not numbered. It will be appreciated that variations from the apparatus and method illustrated in FIG. 3 can be made. Shown is a twin wire former having a layered papermaking headbox 50 which injects or deposits a stream 51 of an aqueous suspension of papermaking fibers onto forming fabric 53 which serves to support and carry the newly-formed wet web 55 downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to transfer fabric 57 traveling at a slower speed than the forming fabric in order to impart increased stretch into the web. Transfer is preferably carried out with the assistance of vacuum shoe 58 such that the forming fabric and the transfer fabric converge and diverge simultaneously at the leading edge of the vacuum slot as described in co-pending application Ser. No. 08/036,649 filed Mar. 24, 1993 in the names of Engel et al. The difference in the respective speeds of the carrier fabrics also beneficially creates slight wrinkling of the fabric. In addition, in order to increase the absorbency of the compressed sheets, it is desirable that the through-fabric have a three-dimensional pattern therein. The pattern of the through-fabric is thereby imparted to the resilient cellulosic sheets. It is believed a variety of patterns are suitable for use with the present invention. Suitable throughdrying fabrics having a three-dimensional contour are described in U.S. Pat. No. 5,429,686 issued Jul. 4, 1995 to Chiu et al. entitled "Apparatus For Making Soft Tissue Products", the entire contents of which are incorporated herein by reference. An exemplary pattern induces a ribbed or "corduroy" like pattern within the fabric extending in the machine direction.

The web is then transferred from the transfer fabric to the throughdrying fabric 59 with the aid of a vacuum transfer roll 60 or a vacuum transfer shoe, optionally again using a fixed gap transfer as previously described. The throughdrying fabric can be traveling at about the same speed or a different speed relative to the transfer fabric. If desired, the throughdrying fabric can be run at a slower speed to further enhance the stretch and contour of the sheet. Transfer is preferably carried out with vacuum assistance to ensure deformation of the sheet to conform to the throughdrying fabric, thus yielding desired bulk and appearance.

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric 59, the web may be dried to a consistency of about 94 percent or greater by throughdryer 61 and thereafter transferred to carrier fabric 62. The dried base sheet 63 is transported to reel 64 using carrier fabric 62 and an optional carrier fabric 65. An optional pressurized turning roll 66 can be used to facilitate transfer of the web from carrier fabric 62 to fabric 65. Suitable carrier fabrics for this purpose are Albany International 84M or 94M and Asten 959 or 937, all of which are relatively smooth fabrics having a fine pattern. The absorbent sheets may subsequently be wound on a winder roll.

Figure 4:
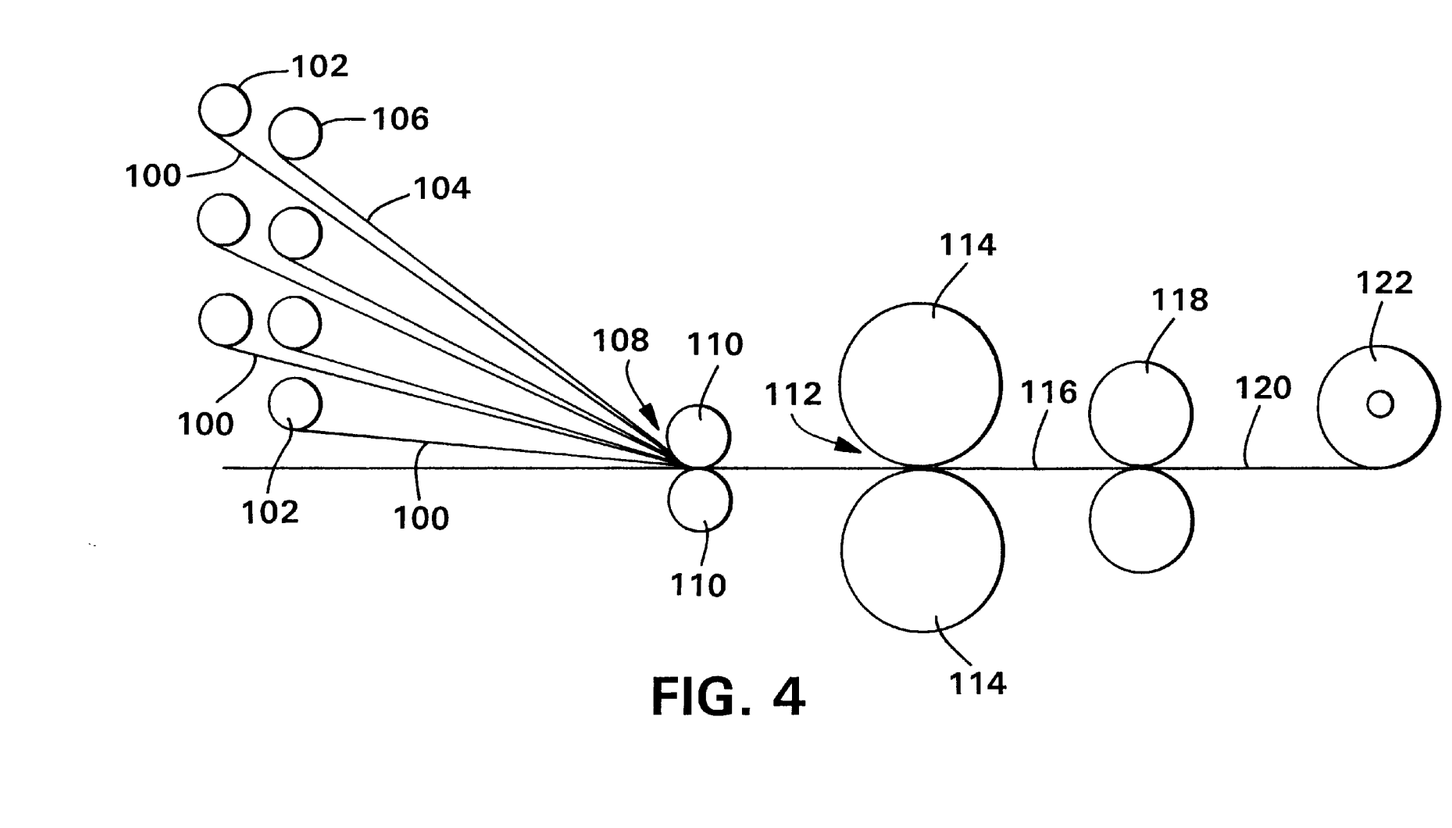
FIG. 4 is a schematic representation of a calendering system useful for making an absorbent pad of the present invention.

As shown in FIG. 4, the desired number of absorbent sheets 100 may then be unwound from a plurality of rolls 102 and superposed with the aid of one or more guide rolls 110. A top insulation sheet layer 104 may be introduced over the absorbent sheets 100 and into nip 108 of guide rolls 110 along with absorbent sheets 100. The top insulating sheet 104 and the plurality of absorbent sheets 100 may then be mechanically compressed when fed through nip 112 formed by calender rolls 114. However, it should be noted that the top insulating sheet 104 may be introduced into the process line before or after calendering. The compressed absorbent sheets together with the insulating layer 116 may then be fed through a mechanical crimper 118. in this regard it should be noted that the top insulating sheet 104 is preferably introduced into the process line such that the knurling of the mechanical crimper contacts the insulation layer 104. The bonded absorbent pad material 120 may then be wound on a winder roll 122. Often the absorbent pad material 120 can be cut or slit to the desired width and the individual slifted sections wound on separate winder rolls. Strips of the absorbent pad material may thereafter be unrolled, cut to the desired length and integrated with packaging as desired.

As used herein "aqueous absorbency" for the purposes of the present invention is determined by the following method:
1. Cut a 4"×6" sample (24 square inch sample); weight the dry sample and record the weight in grams.
   (For free swell testing (0 lbs load) no weight is required. Under load testing a 3 lb. weight equivalent to the sample size is placed on the dry sample)
2. Pour 300 mls of water into the tray. Do not pour the water directly onto the sample. Pour water around the sample.
3. Allow the sample to absorb the water for 1 minute.
4. Lift the sample from the water after 1 minute and tilt platform to remove excess water.
5. Drain for 3 seconds at approximately a 45-degree angle.
6. Weight the wet platform and sample together. Record the weight in grams.
7. Remove the wet sample from the platform and record the wet platform weight in grams.
8. Repeat the test three tifes.
Calculations
Absorbent Capacity in Grams
(Wet Sample+Wet Platform Weight)—(Wet Platform Weight)—(Dry Sample Weight)=Absorbent Capacity in grams
Absorbent Capacity in Gram/Gram
Capacity in Grams/Dry Sample Weight=Absorbent Capacity in gram fluid/gram absorbent material
Absorbent Capacity in Grams/Area
Capacity in Grams/24 Sq. Inches=Capacity in Grams/Sq. Inch.

As used herein the term "bulk" refers to a measure of the thickness of a fabric and which may be determined in accord with ASTM Standard Test Method for Thickness of Nonwoven Fabrics D 5729-95 using a three inch acrylic platen which provides 0.05 psi loading.

As used herein the term "nonwoven" fabric or web means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes.

As used herein the term "spunbonded fibers" refers to small diameter fibers of molecularly oriented polymer. Spunbond fibers are often formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al.

As used herein the term "meltblown fibers" means fine fibers of unoriented polymer. Meltblown fibers are often formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter.

As used herein "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Multilayer laminates may also have various numbers of meltblown layers or multiple spunbond layers in many different configurations and may include other materials like films (F) or coform materials, e.g. SMMS, SM, SFS, etc.

EXAMPLE 1

Sixteen plies of 30 gsm sheets of high yield pulp fibers (bleached chemithermomechanical pulp) were fabricated in accord with Chen '420. The absorbent sheets had a ribbed structure and contained about 1% by weight wet strength agent (Kymene 557H from Hercules, Inc). The absorbent sheets were calendered, together with a 0.005 inch thick polyethylene plastic film at room temperature. The compressed materials were then attached by mechanical crimping using course knurling. The 8 ply pads were mechanically crimped with a pressure of about 3000 pli and the 16 ply pads with a pressure of 4250 pli. The characteristics of the resulting absorbent pads are further described in the tables set forth below.

TABLE I

| Plies | Bulk Reduction | Density (g/cc) | Thickness (cm) | Absorbency (g/fluid) | Calender Load (pli) |
|---|---|---|---|---|---|
| 8 | 0 | 0.051 | 0.528 | 64.87 | — |
| 8 | 56% | 0.109 | 0.231 | 57.48 | 281 |
| 8 | 71% | 0.158 | 0.015 | 52.91 | 633 |
| 8 | 81% | 0.245 | 0.101 | 52.26 | 986 |

TABLE I-continued

| Plies | Bulk Reduction | Density (g/cc) | Thickness (cm) | Absorbency (g/fluid) | Calender Load (pli) |
|---|---|---|---|---|---|
| 8  | 85% | 0.323 | 0.079 | 52.04  | 1515 |
| 16 | 0   | 0.049 | 1.052 | 127.46 | —    |
| 16 | 50% | 0.092 | 0.541 | 110.77 | 281  |
| 16 | 75% | 0.188 | 0.264 | 101.01 | 809  |
| 16 | 80% | 0.233 | 0.216 | 101.14 | 986  |
| 16 | 83% | 0.287 | 0.175 | 98.42  | 1515 |

As may be seen with reference to the above table, although a reduction in absorbency may result from compression of the absorbent sheets, the relationship as between reduced thickness and absorbency is such that highly absorbent pads having excellent absorbent capacity may be achieved. Further, the selection of the number of plies, bulk reduction and compression allows the fabrication of absorbent pads having characteristics specifically tailored to its intended end-use. In particular, it allows for a highly absorbent pads having a ratio of absorbency (g) to bulk well in excess of 2 grams fluid per cubic centimeter.

We claim:

1. An absorbent food pad comprising:
   a film;
   an absorbent core attached to said film, said absorbent core comprising from 3 to 30 sheets of mechanically compressed cellulosic material wherein the mechanically compressed sheets are wet resilient and further wherein the absorbent pad has a bulk less than 0.5 cm, an aqueous absorbent capacity of at least 10 grams fluid per gram absorbent material and further wherein the volume of the absorbent core is capable of expanding at least about 50% in volume, relative to the dry volume, upon wetting; and
   wherein said absorbent core absorbs and retains standing fluids when food rests upon said film.

2. The absorbent pad of claim 1 wherein said mechanically compressed sheets have a basis weight of between about 20 and 40 gsm.

3. The absorbent pad of claim 2 wherein said mechanically compressed sheets contain a three-dimensional pattern.

4. The absorbent pad of claim 2, wherein said absorbent core has an aqueous absorbent capacity of at least about 13 grams fluid per gram absorbent material.

5. The absorbent pad of claim 1 wherein said cellulosic material comprises a high yield pulp fiber and a wet strength agent.

6. The absorbent pad of claim 5 wherein said mechanically compressed sheets have a three-dimensional pattern therein.

7. The absorbent pad of claim 1 wherein the volume of said absorbent core expands at least about 100%, relative to the dry volume, upon wetting.

8. The absorbent pad of claim 1 wherein the volume of said absorbent core expands at least about 150%, relative to the dry volume, upon wetting.

9. The absorbent pad of claim 7 wherein said absorbent pad has an aqueous absorbent capacity of at least about 15 grams fluid per gram absorbent material.

10. The absorbent pad of claim 1 wherein said absorbent core has an absorbent capacity of at least 13 grams fluid per gram absorbent material and wherein said absorbent pad has a bulk of less than 0.38 cm.

11. The absorbent pad of claim 1 wherein said absorbent pad has a bulk of less than 0.38 centimeter and a ratio of absorbent capacity to bulk of at least 1.3 grams fluid per cubic centimeter.

12. The absorbent pad of claim 1 having a bulk of less than 0.3 centimeter and a ratio of absorbent capacity to volume of at least 1.8 grams fluid per cubic centimeter.

13. The absorbent pad of claim 1 wherein the volume of said absorbent pad expands substantially in bulk upon absorbing fluid.

14. The absorbent pad of claim 1 wherein said film is a liquid impervious film.

15. The absorbent pad of claim 1 wherein said film is adhesively bonded to said absorbent core.

16. The absorbent pad of claim 1 wherein said film is fixedly attached to said absorbent core by mechanical crimping.

17. An absorbent pad for a food product comprising:
    a film;
    an absorbent core attached to said film, said absorbent core comprising a plurality of wet resilient sheets of mechanically compressed cellulosic material wherein said absorbent core has an absorbent capacity of at least 0.90 grams fluid per square centimeter and wherein the absorbent pad has a bulk of less than about 0.5 cm; and
    wherein said absorbent core absorbs and retains standing fluids when said food product rests upon said film.

18. The absorbent pad of claim 17 wherein said absorbent pad has a thickness of 0.38 cm or less, an area of 130 cm$^2$ or less and absorbs at least about 100 g fluid.

19. The absorbent pad of claim 17 wherein said pad has a bulk of less than 0.38 cm.

20. The absorbent pad of claim 17 wherein said pad has a bulk of less than about 0.3 cm.

21. The absorbent pad of claim 17 wherein said absorbent pad retains at least about 70% of said absorbent capacity under a load of 1.36 Kg.

22. The absorbent pad of claim 17 wherein said absorbent core comprises at least 3 sheets of mechanically compressed cellulosic material.

23. The absorbent pad of claim 22 wherein said film is a liquid impervious film.

24. The absorbent pad of claim 22 wherein said film is adhesively bonded to said absorbent core.

25. The absorbent pad of claim 22 wherein said film is fixedly attached to said absorbent core by mechanical crimping.

* * * * *